United States Patent [19]

Richter et al.

[11] 4,154,931

[45] May 15, 1979

[54] PROCESS FOR THE PREPARATION OF CYCLIC UREAS

[75] Inventors: Reinhard H. Richter, North Haven; Benjamin W. Tucker, Bethany; Henri Ulrich, Northford, all of Conn.

[73] Assignee: The Upjohn Company, Kalamazoo, Mich.

[21] Appl. No.: 875,182

[22] Filed: Feb. 6, 1978

[51] Int. Cl.² ............................................. C07D 239/04
[52] U.S. Cl. .............................. 544/315; 260/239.3 A; 548/317; 548/319; 548/322
[58] Field of Search ................ 544/315; 548/317, 319, 548/322; 260/239.3 A, 239.3 R

[56] References Cited

U.S. PATENT DOCUMENTS

| 3,137,697 | 6/1964 | Boswell et al. | 544/315 |
| 3,158,501 | 11/1964 | Wayland | 544/315 |
| 4,041,222 | 8/1971 | Schoeppel et al. | 544/315 |

Primary Examiner—Nicholas S. Rizzo
Attorney, Agent, or Firm—James S. Rose; Denis A. Firth

[57] ABSTRACT

A novel process is disclosed for the preparation of cyclic ureas having the formula

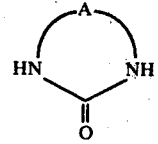

wherein A is a straight chain alkylene radical of 2 to 4 carbon atoms, inclusive, wherein said alkylene radical can be substituted by at least one member selected from the group consisting of halogen, lower alkyl, lower alkoxy, aryl, aryloxy, aralkyl, and cycloaklyl. An alkylene diamine having the formula $NH_2ANH_2$, wherein A is defined as above, is reacted in a solvent with carbonyl sulfide to form the corresponding N-(ω-aminoalkyl)thiocarbamic acid ($NH_2ANHCOSH$) or zwitterion thereof. The thiocarbamic acid is then heated to form the cyclic urea.

The cyclic ureas are useful as cross-linkers and extenders in polyurethane formulations, and those ureas having 4 carbons in the alkylene chain find particular utility in the production of bis cyclic ureas which serve as masked isocyanate compounds in one-component polyurethane elastomer formulations.

6 Claims, No Drawings

PROCESS FOR THE PREPARATION OF CYCLIC UREAS

BACKGROUND OF THE INVENTION

1. Field of the Invention

This invention relates to the preparation of ureas, and, more particularly, is concerned with a novel process for the preparation of cyclic alkylene ureas and novel intermediates therefor.

2. Description of the Prior Art

The preparation of cyclic alkylene ureas is well known in the art and a number of different procedures have been described. Illustratively, alkylene diamines can be reacted with carbon dioxide to form the corresponding alkylene urea but high temperatures and pressures are required; see Ind. Eng. Chem. 1948, 40, 393. In a more classic reaction, phosgene is reacted with an alkylene diamine to form the urea (see Annalen, 1937, 532, 300) but the disadvantage in this procedure is the commercially unacceptable high weight loss arising from the two chlorine atoms in addition to low product yield due to losses from polymer forming side reactions.

Other routes to cyclic ureas have been found but these require a number of cost increasing or cumbersome steps to reach the product. For example, lactam oximes can be rearranged to cyclic ureas by polyphosphoric acid as noted by Behringer et al (Annalen, 1957, 607, 67); LeBerre et al (Bull Soc. Chim. 9, 3245, 1971) have found that the p-toluenesulfonate ester derivative of a lactam oxime can be rearranged to the urea by treatment with base.

The preparation of cyclic alkylene thioureas has been described, see Organic Syntheses 26, 34, or Arya et al, Indian Journal of Chemistry, 14B, p. 773, 1976. However, the conversion of the thiourea to the corresponding urea requires an expensive oxidation step.

Unexpectedly, we have found that certain species of cyclic alkylene ureas can be prepared via a novel process which overcomes both of the prior art problems of multi-step syntheses and expensive oxidation steps. Moreover, our novel process provides an additional benefit in terms of both unit processing and unit operation because the whole process can be carried out in the same reaction vessel without the need for the isolation of intermediates.

SUMMARY OF THE INVENTION

This invention comprises a process for the preparation of a cyclic urea having the formula

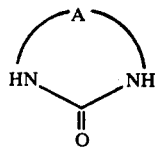

I wherein A is a straight chain alkylene radical of 2 to 4 carbon atoms, inclusive, wherein said alkylene radical can be substituted by at least one member selected from the group consisting of halogen, lower-alkyl, lower-alkoxy, aryl, aryloxy, aralkyl, and cycloalkyl comprising the steps of:

(a) reacting in a solvent an alkylene diamine having the formula $NH_2ANH_2$ wherein A is defined as above with carbonyl sulfide to form the corresponding N-($\omega$-aminoalkyl)thiocarbamic acid or zwitterion thereof; and (b) heating said thiocarbamic acid or zwitterion thereof to form said cyclic urea.

This invention also comprises the thiocarbamic acid intermediates above having the formula $$NH_2ANHCOSH \qquad II$$

or zwitterion thereof, wherein A is as defined above.

The term "zwitterion" means a dipolar ion or inner salt in equilibrium with said thiocarbamic acid (II) and having the formula $$^{\oplus}NH_3ANHCOS^{\ominus} \qquad III$$

For a discussion of zwitterion or inner salt formation in amino acids see E. Wertheim's Textbook of Organic Chemistry, 1945, p. 245, The Blakiston Co., Philadelphia, Pa.

The term "halogen" means fluorine, chlorine, bromine, and iodine.

The term "straight chain alkylene from 2 to 4 carbon atoms" means $-CH_2CH_2-$, $-CH_2CH_2CH_2-$, and $-CH_2CH_2CH_2CH_2-$.

The term "lower-alkyl" means alkyl having from 1 to 8 carbon atoms, inclusive, such as methyl, ethyl, propyl, butyl, pentyl, hexyl, heptyl, octyl, and isomeric forms thereof.

The term "lower-alkoxy" means alkoxy having from 1 to 8 carbon atoms, inclusive, such as methoxy, ethoxy, propoxy, butoxy, pentoxy, hexoxy, heptoxy, octoxy, and isomeric forms thereof.

The term "aryl" means the radical obtained by removing one nuclear hydrogen atom from an aromatic hydrocarbon having from 6 to 12 carbon atoms, inclusive, such as phenyl, tolyl, xylyl, naphthyl, biphenylyl, and the like.

The term "aryloxy" means a radical obtained by removing the phenolic hydrogen atom from a hydroxyaryl compound wherein aryl is defined as above and is inclusive of phenoxy, lower-alkyl substituted phenoxy, naphthoxy, lower-alkyl substituted naphthoxy, diphenylyloxy, and the like.

The term "aralkyl" means the radical obtained by removing one alkyl hydrogen from an aryl substituted lower alkane wherein aryl and lower-alkane have the same carbon atom limitations set forth above for aryl and lower-alkyl respectively and is inclusive of benzyl, p-methylbenzyl, p-ethylbenzyl, $\beta$-phenylethyl, benzhydryl, naphthylmethyl, and the like.

The term "cycloalkyl" means the radical obtained by removing one hydrogen atom from a ring carbon atom of a cycloaliphatic hydrocarbon having from 3 to 8 carbon atoms, inclusive. Illustrative of cycloalkyl are cyclopropyl, cyclobutyl, cyclopentyl, cyclohexyl, methylcyclohexyl, cycloheptyl, cyclooctyl, and the like.

The cyclic ureas (I) prepared in accordance with the present process are useful as extenders and cross-linking agents in polyurethane elastomer materials. Those cyclic ureas which contain 4 carbon atoms in succession in the chain find particular utility in the preparation of the corresponding novel bis cyclic ureas which are disclosed in copending application Ser. No. 754,189 filed Dec. 27, 1976 and which are used as masked diisocyanates in one-component polyurethane systems useful in elastomers, coatings, fibers, and adhesives.

The novel thiocarbamic acids (II, or III) produced in accordance with the present process are used, inter alia, as the precursors for the cyclic ureas (I).

DETAILED DESCRIPTION OF THE INVENTION

The novel process in accordance with the present invention is represented schematically by the following equation

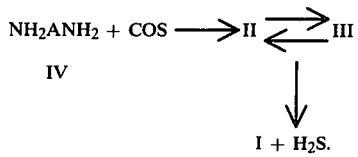

$$NH_2ANH_2 + COS \longrightarrow II \rightleftarrows III$$
$$IV$$
$$\downarrow$$
$$I + H_2S.$$

The alkylene diamine (IV) is reacted in a solvent with carbonyl sulfide to form the novel N-($\omega$-aminoalkyl) thiocarbamic acid (II) which is in equilibrium with its zwitterion (III) and which zwitterion is otherwise known in the art as a dipolar ion or inner salt as defined hereinbefore. Heating of the solution of the thiocarbamic acid (II) or zwitterion thereof (III) produces the cyclic urea (I).

A critical feature of the present invention is the number of carbons which separate the two amine groups in IV. The number of those atoms must be at least 2 but no more than 4 in order to obtain the cyclic ureas (I) in accordance with the present process. When a diamine having 5 or more carbon atoms in the chain is reacted with carbonyl sulfide the thiocarbamic acid (II) or switterion (III) thereof is obtained but cannot be cyclized to the urea.

Illustrative of the diamines used in the present process are ethylene diamine(1,2-ethylene diamine), propylene diamine(1,3-trimethylene diamine), butylene diamine(1,4-tetramethylene diamine), 1,3-isobutylene diamine, 1,4-isopentylene diamine, 2-ethyl-1,4-butylene diamine, and the like; 2-chloro-1,4-tetramethylene diamine, 2-bromo-1,4-tetramethylene diamine, 2-methoxy-1,4-tetramethylene diamine, 2-butoxy-1,4-tetramethylene diamine, 2-phenyl-1,3-propylene diamine, 2-tolyl-1,3-propylene diamine, 2-phenyl-1,4-tetramethylene diamine, 2-phenoxy-1,3-propylene diamine, 2-benzyl-1,3-propylene diamine, 2-benzyl-1,4-tetramethylene diamine, 2-($\beta$-phenylethyl)-1,3-propylene diamine, 2-($\beta$-phenylethyl)-1,4-tetramethylene diamine, 2-cyclobutyl-1,4-tetramethylene diamine, 2-cyclopentyl-1,4-tetramethylene diamine, 2-cyclohexyl-1,4-tetramethylene diamine, and the like.

A preferred class of alkylene diamines comprises those wherein A is an unsubstituted alkylene radical of 2 to 4 carbon atoms, inclusive, namely ethylene diamine, propylene diamine, and butylene diamine. A most preferred diamine is butylene diamine.

The solvent for carrying out the reaction of (IV) with carbonyl sulfide is an inert organic solvent and the choice is not critical so long as the solvent contains no groups which may interact with the reactants and products and so long as it can solubilize both the reactants and products. Illustrative of classes of solvents useful in the present process are the lower alkanols; the alkylene glycols wherein alkylene is $C_2$ to $C_4$ and ether derivatives thereof; the polar (dielectric constant of at least 5) halogenated hydrocarbon solvents having a lower-alkane backbone and substituted by fluorine, chlorine, bromine, or iodine; the five and six membered cycloaliphatic ethers; the dipolar aprotic solvents; the polar (dielectric constant of at least 5) aromatic solvents; mixtures of solvents chosen from the above classes; and mixtures of solvents from the above types which are miscible with water in combination therewith in varying proportions in parts by weight of from about 1:4 to about 4:1 parts of water to parts of solvent, preferably from 1:3 to 3:1, and most preferably 1:1.

Illustrative examples from the classes of solvents set forth above are methanol, ethanol, propanol, butanol, pentanol, hexanol, heptanol, octanol, isopropanol, isobutanol, 2,3-dimethylbutanol; ethylene glycol, diethylene glycol, propylene glycol, monomethyl ether of ethylene glycol, monobutyl ether of ethylene glycol, monoethyl ether of diethylene glycol, monomethyl ether of diethylene glycol, dimethyl ether of diethylene glycol, dimethyl ether of ethylene glycol; chloroform, tetrachloroethane, 1,2-dichloroethane, bromoform, bromotrichloromethane; 1,4-dioxane, tetrahydrofuran; dimethylformamide, dimethylacetamide, dimethyl sulfoxide, tetramethylene sulfone; chlorobenzene, orthodichlorobenzene, nitrobenzene; mixtures of methanol and water, ethanol and water, dioxane and water, tetrahydrofuran and water, and the like.

A preferred mixed solvent is ethanol and water mixed in equal proportions by weight.

The carbonyl sulfide is reacted with the diamine (IV) in solution using any suitable reaction vessel for carrying out the reaction. Advantageously the vessel is equipped with means for adding a gaseous reactant to the vessel, means for stirring or agitating the contents of the vessel, as well as means for venting or allowing for the return of refluxing liquid back to the vessel, and means for heating and/or cooling said vessel.

The carbonyl sulfide is gaseous and may be bubbled directly into the solution of the diamine, or, alternatively, dissolved in a solvent, preferably the same solvent used to dissolve the diamine, and its solution added to the reaction vessel. The amount of carbonyl sulfide employed per mole of diamine is not critical; however, in order to optimize the yield of thiocarbamic acid or zwitterion, the carbonyl sulfide should be present in at least a molar equivalent amount and preferably in an excess of from about 1.02 mole to about 1.10 mole per mole of diamine.

Preferably, the gaseous carbonyl sulfide is passed into the diamine solution, using any suitable means known to those skilled in the art for the distribution and admixture of a gas into a liquid system, until the desired weight increase due to absorbed gas is observed in the reaction mixture. Illustratively, the gas can be sparged through an open ended dip tube or a dip tube fitted with a fritted disc or other dispersing means known to those skilled in the art.

Generally speaking, the reaction of carbonyl sulfide with the diamine is exothermic and, in one embodiment of the present process, the reaction can be allowed to proceed without external heating if the rate of addition of the carbonyl sulfide is adjusted so that the temperature of the reaction solution does not rise to undesirably high levels where excessive reflux would occur. Obviously, the temperature of reflux depends upon the boiling point of the solvent employed. In a preferred but not limiting embodiment of the process in accordance with the present invention the gas is added to the diamine solution at a reaction temperature of from about 20° C. to about 75° C., and preferably 30° C. to about 50° C.

This temperature range, depending on the boiling point of the solvent employed, is maintained either by reaction exotherm or by the application of external heat using any suitable heating means known to those skilled in the art.

Accordingly, the duration of the heating period is not a critical feature but is dependent upon the actual temperature used. One skilled in the art can easily determine the completion of the reaction either by simple trial and error or by testing the reaction solution using any convenient and appropriate analytical procedure. Illustratively, the reaction mixture is analyzed by infrared absorption analysis. The point at which the normal N-H absorption bands of the starting diamine completely disappear signifies the termination of the reaction.

Generally speaking, this reaction period falls within the range of from about 0.25 hour to about 8.0 hours, preferably from about 0.5 hour to about 4.0 hours.

Amongst the unexpected and advantageous aspects of the present process are the mild reaction conditions under which the novel thiocarbamic acid products are formed.

While not wishing the present invention to be bound by any theoretical considerations but only by the claims appended hereinbelow, it is believed that the thiocarbamic acid (II) exists primarily in the zwitterionic form (III) particularly when in the solid state or in neutral solution.

The thiocarbamic acids (II) or zwitterions thereof can be easily isolated in their pure solid form from the reaction solutions described above simply by adding a non-solvent for the product to the reaction solutions obtained above which results in precipitation of the desired acid. The solid can be isolated using standard isolation procedures known to those skilled in the art such as filtration, centrifugation, and the like.

Typical non-solvents useful for the precipitation of the thiocarbamic acids or zwitterions thereof are benzene, toluene, xylene, carbon tetrachloride, or any other non-solvent found suitable for this application.

The intermediate thiocarbamic acids or zwitterions thereof isolated in pure form as described above are easily converted to the desired ureas (I) simply by heating. In a preferred method the intermediate is heated in the presence of a solvent and in a most preferred method the intermediate is dissolved in one of the reaction solvents described above and heated until no more hydrogen sulfide gas is evolved.

Advantageously, and in a most preferred embodiment of the process in accordance with the present invention, the thiocarbamic acids are not isolated from their original reaction solutions but rather are left therein and converted directly to the corresponding cyclic ureas by heating said solutions.

This feature, which allows the whole reaction process to be carried out without the need for isolating or purifying intermediates, greatly simplifies the procedure in accordance with the present invention over prior art methods.

The temperature, to which a solution containing the thiocarbamic acid should be heated to obtain optimum conversion to the corresponding cyclic ureas, is governed by the choice of reaction solvent and its boiling point or reflux temperature. However, the optimum temperature in any particular instance is readily determined by one skilled in the art by trial and error.

Advantageously, the solution of thiocarbamic acid or zwitterion thereof can be heated at a temperature of from about 50° C. to about 150° C., preferably from about 50° C. to about 100° C.

The duration of the heating period is not critical and the optimum time can be easily determined by trial and error. If maximum conversion to cyclic urea is desired then the solution is simply heated until the evolution of hydrogen sulfide reaction by-product ceases. Alternatively, one skilled in the art can analyze aliquot samples of the solution during the reaction by appropriate means such as infrared absorption spectroscopy for characteristic absorption peaks due to the thiocarbamic acid or zwitterion thereof. The disappearance of these characteristic peaks marks the completion of the reaction.

Generally speaking, the heating period for converting the thiocarbamic acid to the urea is from about 0.5 hour to about 24 hours, preferably from about 1 hour to about 8 hours.

In a particularly preferred embodiment of the present process a catalytic amount of an acid having a $pK_a$ value (where $pK_a$ is the negative logarithm of the acid ionization constant) in aqueous medium below about 2 is added to the solution of said thiocarbamic acid or zwitterion thereof and thereafter the acidified solution is heated in accordance with the procedure described above to form the cyclic urea.

By catalytic amount is meant the amount determined by one skilled in the art which gives rise to an acceleration in the formation of the urea, or, in the alternative, gives rise to lower reaction temperatures. Generally speaking, the amount of acid employed advantageously falls within the range of about 1 mole percent to about 15 mole percent per mole of thiocarbamic acid and preferably from about 2 to about 10 mole percent.

Acids having a $pK_a$ value below about 2 are generally regarded as embracing the moderate to strong acids and included in this class are such strong inorganic acids as hydrochloric, phosphoric, phosphorous, sulfuric, nitric, hypophosphorous, and the like. Typical of the strong organic acids are aniline-3-sulfonic, aniline-4-sulfonic, benzenesulfonic, p-toluenesulfonic, chloromethyl phosphoric, 4-chlorophenyl phosphoric, and the like.

A preferred group of acids comprises hydrochloric, benzenesulfonic, and p-toluenesulfonic. A most preferred acid is hydrochloric.

The cyclic ureas present in the reaction solution are easily separated therefrom and isolated in pure form using standard separation techniques known to those skilled in the art. Preferably the urea separates out as a crystalline solid upon cooling of the reaction solution and is isolated in pure form by filtration. In the event the urea remains in solution, it can be isolated by concentrating the solution either in vacuo or at atmospheric pressure and triturating the remaining moist residue in a suitable crystallizing medium such as methanol, ethanol, isopropanol, dioxane, acetone, acetonitrile, or any suitable solvent found by trial and error to be useful in forming the crystalline urea. Alternatively, the urea can be extracted in a suitable solvent using either solid-liquid extraction or liquid-liquid extraction. Evaporation of the solvent provides the pure product. If further purification is desired then sublimation or crystallization or other suitable means for the purification of solids can be employed.

The following examples describe the manner and process of making and using the invention and set forth the best mode contemplated by the inventors of carrying out the invention but are not to be construed as limiting.

EXAMPLE 1

A one liter round bottom flask equipped with a stirrer, a dry ice-acetone reflux condenser, gas inlet tube, and thermometer was charged with 88 g. (1 mole) of 1,4-tetramethylene diamine dissolved in a mixture of 250 ml. of water and 250 ml. of ethanol. A cylinder of carbonyl sulfide gas was placed on a weighing scale and the cylinder valve connected to the gas inlet tube.

The carbonyl sulfide gas was passed under the surface of the diamine solution during continual stirring starting at a solution temperature of 32° C. The loss in weight of the gas cylinder was recorded and after an 80 minute addition period 62.5 g. (1.04 moles) had been passed into the reaction solution whereupon the flow was stopped. The solution temperature had risen to 44.8° C. and the first sign of carbonyl sulfide reflux from the condenser was observed.

Stirring of the solution was continued for 1 hour whereupon it cooled down to 34° C. and crystalline solid (the zwitterion of N-[4-aminobutyl]thiocarbamic acid) began to form in the flask. A heating bath was applied and stirring continued. At 60° C. 8 g. of concentrated hydrochloric acid was added slowly and after about 15 minutes the temperature of the solution was 73° C. with solvent reflux. Also hydrogen sulfide gas began to evolve. Approximately 1 hour later the reaction temperature was 78° C. and all solid had dissolved. The heating was stopped when the temperature had reached 83° C. which was 3.5 hours after heating was begun.

The solution was cooled to about 10° C., filtered to remove a small amount (0.8 g.) of the high melting intermediate thiocarbamic acid and then concentrated on a rotary evaporator to yield a solid residue. The residue was dissolved in 300 ml. of hot water followed by extraction with 300 ml. of chloroform in a liquid-liquid extractor. Evaporation of the chloroform provided 62.2 g. of tetramethylene urea; m.p. 157°–164° C.

A second extraction of the aqueous solution with 300 ml. of chloroform provided 14.9 g. of the urea. A third chloroform extraction yielded 7.5 g. of a liquid residue which was discarded.

The two crops of solid product were combined and processed in a sublimator at about 0.1 mm of Hg pressure using a heating source at 150°–190° C. to provide 67 g. (59% yield) of sublimed tetramethylene urea; m.p. 166°–170° C. (cf. authentic material m.p. 172° C.). The product was also authenticated by infrared analysis.

EXAMPLE 2

A 500 ml. flask equipped according to Example 1 was charged with 30 g. (0.5 mole) of ethylene diamine dissolved in a mixture of 125 ml. of ethanol and 125 ml. of water.

Carbonyl sulfide was passed into the diamine solution starting at a solution temperature of 35° C. After 40 minutes the solution temperature had risen to 41° C. and 30 g. (0.5 mole) of carbonyl sulfide has been passed into the solution. An additional 2 g. of carbonyl sulfide was added before the gas flow was stopped.

Upon cooling the solution the zwitterion salt precipitated out. A sample of approximately 1 g. of the crystalline material was collected by filtration, washed with ethanol, and dried. The solid decomposed at 142° C. with evolution of hydrogen sulfide gas and corresponded to the following structure

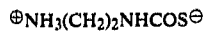

Anal: calcd. for $C_3H_8N_2OS$: C, 29.98%; H, 6.71%; N, 23.31%. Found: C, 29.93%; H, 6.90%; N, 23.43%.

A heating bath was applied to the reaction flask containing the remaining bulk of the precipitated salt obtained above and stirring was resumed. Two ml. of concentrated hydrochloric acid was added slowly at a temperature of about 50° C. After about 0.5 hour of heating (temperature=74° C.) solution reflux and hydrogen sulfide evolution began. In approximately 1 hour, all the precipitated solid had dissolved. Heating was continued for approximately 2.75 hours and with a nitrogen purge for about the last 15 minutes of the heating period. The solution was cooled to below 5° C. without any crystallization occurring.

Concentration of the solution on a rotary evaporator under vacuum provided 41.3 g. of residue. The residue was triturated in acetone and filtered to yield crystalline ethylene urea; wt.=18.5 g.; m.p. 127°–130° C. The product was also verified by infrared comparison with an authentic sample. The urea was recrystallized from acetone, m.p. 129°–131° C. then sublimed at 120°–150° C./0.1 mm., m.p. 129°–131° C. (cf. authentic material m.p. 129° C.); yield was 17.7 g. (42% of theory).

EXAMPLE 3

A 500 ml. flask equipped according to Example 1 was charged with 37 g. (0.5 mole) of 1,3-propylene diamine dissolved in a mixture of 125 ml. of ethanol and 125 ml. of water.

Carbonyl sulfide was passed into the diamine solution starting at a solution temperature of 32° C. After 55 minutes the solution temperature had risen to 41° C. and 30 g. (0.5 mole) of carbonyl sulfide had been passed into the solution. An additional 2 g. of carbonyl sulfide was added before the flow was stopped.

Upon cooling the solution the zwitterion salt precipitated. A sample of approximately 3 g. of the crystalline material was collected by filtration, washed with ethanol, and dried. The solid started to turn yellow at about 130° C. and melted at 260°–266° C. (propylene urea melting range); hydrogen sulfide was evolved during the heating; the salt corresponded to the following structure

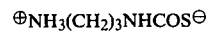

Anal: calcd. for $C_4H_{10}N_2OS$: C, 35.80%; H, 7.51%; N, 20.87%. Found: C, 35.76%; H, 7.70%, N, 20.75%.

A heating bath was applied to the reaction flask containing the remaining bulk of the precipitated salt and stirring was resumed. After about 20 minutes the solution temperature was 67° C. and 1.6 g. of concentrated hydrochloric acid was added slowly. At 76° C. (in about 40 minutes) all the precipitated solid had dissolved. After about 1.5 hours the reaction temperature was 84° C. and heating was discontinued.

The solution was cooled to about 1° C. whereupon a solid precipitated which was collected by filtration, washed in ethanol and dried to provide 30.2 g. of propylene urea; m.p. 263°–266° C. The filtrate was concentrated in a rotary evaporator under vacuum to provide 23.9 g. of residue. Trituration of the residue in ethanol followed by filtration yielded an impure crystalline solid. The solid was dissolved in 500 ml. of hot isopropyl alcohol. The isopropyl alcohol solution was decanted while still hot from a small amount of insoluble residue. Cooling of the solution resulted in the precipitation of a further crop of crystalline propylene urea which was collected by filtration and dried; wt., 10.5 g.; m.p. 255°–263° C.

The two crops of propylene urea were combined and sublimed at 150°–200° C./0.1 mm. to yield 38.6 g. (81% yield) of pure propylene urea m.p. 263°–266° C.

EXAMPLE 4

The following exemplifies the conversion of a zwitterion salt to the corresponding cyclic urea in the absence of catalyst in accordance with the present invention.

A 1 g. sample of the zwitterion salt isolated in Example 3 was mixed with 20 ml. of chlorobenzene in a 100 ml. reaction flask fitted with a stirrer, reflux condenser, and thermometer. The salt was not soluble in the chlorobenzene at room temperature.

The mixture was stirred and heated and after about 20 minutes the solution temperature was 128° C. with reflux and hydrogen sulfide evolution. When 1 hour and 20 minutes had elapsed the solution was clear and the temperature was 133° C. Heating was stopped, the solution cooled and crystalline propylene urea collected, m.p. 261°–263° C.; sample authenticated by infrared analysis.

We claim:

1. A process for the preparation of a cyclic urea having the formula

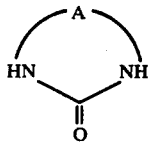

wherein A is a straight chain alkylene radical of 2 to 4 carbon atoms, inclusive, wherein said alkylene radical can be substituted by at least one member selected from the group consisting of halogen, lower alkyl, lower alkoxy, aryl, aryloxy, aralkyl, and cycloalkyl, comprising the steps of:

(a) reacting in a solvent at a reaction temperature of from about 20° C. to about 75° C. an alkylene diamine having the formula $NH_2ANH_2$, wherein A is defined as above, with carbonyl sulfide to form the corresponding N-(ω-aminoalkyl)thiocarbamic acid or zwitterion thereof; and (b) heating said thiocarbamic acid or zwitterion thereof at a temperature of from about 50° C. to about 150° C. to form said cyclic urea.

2. A process according to claim 1 wherein said carbonyl sulfide is reacted with said alkylene diamine by passing said carbonyl sulfide gas into a solution of said diamine at an elevated temperature.

3. A process according to claim 1 wherein step (b) is carried out in the presence of a catalytic amount of an acid having a $pK_a$ value, in aqueous medium, below about 2.

4. A process for the preparation of a cyclic urea having the formula

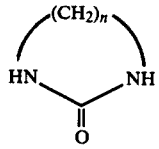

wherein n is an integer from 2 to 4 inclusive comprising the steps of:

(a) passing carbonyl sulfide gas into a solution of an alkylene diamine having the formula $NH_2(CH_2)_nNH_2$ wherein n is defined as above at a temperature of from about 20° to about 75° C. to form the corresponding N-(ω-aminoalkyl)thiocarbamic acid or zwitterion thereof; and (b) heating said thiocarbamic acid or zwitterion thereof in solution at a temperature of about 50° to about 150° C. to form said cyclic urea.

5. A process according to claim 4 wherein step (b) is carried out in the presence of a catalytic amount of an acid having a $pK_a$ value in aqueous medium below about 2.

6. A process for the preparation of tetramethylene urea comprising the steps of:

(a) passing carbonyl sulfide gas into a solution of tetramethylene diamine dissolved in a mixture of water and ethanol in equal proportions by weight at a temperature of from about 30° C. to about 45° C. to form N-(4-aminobutyl)thiocarbamic acid or zwitterion thereof; and (b) heating said thiocarbamic acid or zwitterion thereof in said mixture of water and ethanol at a temperature from about 60° to about 85° C. in the presence of a catalytic amount of concentrated hydrochloric acid to form said tetramethylene urea.

* * * * *

Disclaimer 4,154,931.—*Reinhard H. Richter*, North Haven, *Benjamin W. Tucker*, Bethany, and *Henri Ulrich*, Northford, Conn. PROCESS FOR THE PREPARATION OF CYCLIC UREAS. Patent dated May 15, 1979. Disclaimer filed Jan. 24, 1980, by the assignee, *The Upjohn Company*.

Hereby enters this disclaimer to claims 1 through 6 inclusive, of said patent.
[*Official Gazette March 11, 1980.*]